(12) United States Patent
Cho et al.

(10) Patent No.: US 8,795,393 B2
(45) Date of Patent: Aug. 5, 2014

(54) METHOD FOR PRODUCING BIOFUEL USING MARINE ALGAE-DERIVED GALACTAN

(75) Inventors: Jin-Ku Cho, Gyeonggi-do (KR); Sang-Yong Kim, Chungcheongnam-do (KR); Do-Hoon Lee, Seoul (KR); Bo-Ra Kim, Daejeon (KR); Jae-Won Jung, Seoul (KR)

(73) Assignee: Korea Institute of Industrial Technology, Chungcheongnam-do (KR)

( * ) Notice: Subject to any disclaimer, the term of this patent is extended or adjusted under 35 U.S.C. 154(b) by 109 days.

(21) Appl. No.: 13/320,058

(22) PCT Filed: Apr. 15, 2010

(86) PCT No.: PCT/KR2010/002360
§ 371 (c)(1),
(2), (4) Date: Nov. 11, 2011

(87) PCT Pub. No.: WO2010/131844
PCT Pub. Date: Nov. 18, 2010

(65) Prior Publication Data
US 2012/0053355 A1    Mar. 1, 2012

(30) Foreign Application Priority Data

May 11, 2009   (KR) .................... 10-2009-0040576
Aug. 12, 2009  (KR) .................... 10-2009-0074234
Aug. 12, 2009  (KR) .................... 10-2009-0074245

(51) Int. Cl.
*C10L 1/18*     (2006.01)
*C07C 69/66*    (2006.01)
*C07D 307/50*   (2006.01)

(52) U.S. Cl.
USPC ............... 44/350; 44/400; 549/488; 560/174

(58) Field of Classification Search
USPC .................... 44/350, 400; 560/174; 549/488
See application file for complete search history.

(56) References Cited

U.S. PATENT DOCUMENTS

2010/0218416 A1*  9/2010  Gruter ........................ 44/350

FOREIGN PATENT DOCUMENTS

| JP | 55053280 A | 4/1980 |
| JP | 2005521748 A | 7/2005 |
| KR | 100882462 | 2/2009 |
| WO | WO 2007104514 A | 9/2007 |
| WO | WO 2007104514 A2 | 9/2007 |
| WO | WO 2008105618 A1 | 9/2008 |
| WO | WO 2009030506 A2 | 3/2009 |
| WO | WO 2009030506 A3 | 3/2009 |
| WO | WO 2009030511 A1 | 3/2009 |

OTHER PUBLICATIONS

Smith et al, Canadian J. of Chemistry, vol. 33, p. 1352-1360 (1955).*
Abstract of Chinese Patent—CN101400666, Apr. 1, 2009, 1 page.

(Continued)

*Primary Examiner* — T. Victor Oh
(74) *Attorney, Agent, or Firm* — Dority & Manning, P.A.

(57) ABSTRACT

Disclosed is a method of preparing a petroleum-alternative bio fuel material such as 5-hydroxymethyl-2-furfural (HMF), 5-alkoxymethyl-2-furfural, levulinic acid alkil ester, etc. through a single process without saccharification, using a catalyst conversion reaction, from galactan that can be massively supplied at low costs and extracted from macroalgae of marine reusable resources.
Thus, the macroalgae of the marine biomass resources is used so that a carbon source can be more easily extracted than that of a lignocellulosic biomass resource without a problem of having an effect on grain price like a crop-based biomass.

12 Claims, 7 Drawing Sheets

(56) References Cited

OTHER PUBLICATIONS

Article—A. N. O'Neill, "3,6-Anhydro-D-galactose as a Constituent of K-Carrageenin," *J Am. Chem. Soc.*, vol.77, 1955, pp. 2837-2839.
Article—Kim et al., "Facile Single-Step conversion of Macroalgal Polymeric Carbohydrates into Biofuels," *Chem. Sus. Chem.*, vol. 3, 2010, pp. 1273-1275.
Articie—Zhao, et al,, "Metal Chlorides in Ionic Liquid Solvents Convert Sugars to 5-Hydromethylfurfural," *Science*, vol. 316, Jun. 15, 2007, pp. 1597-1600.
Search Report for PCT/KR2010/002360 dated Jan. 31, 2011, 3 pages.
Abstract of Japanese Patent—JP2007145736, Jun. 14, 2007, 2 pages.

\* cited by examiner

METHOD FOR PRODUCING BIOFUEL USING MARINE ALGAE-DERIVED GALACTAN

CROSS REFERENCE TO RELATED APPLICATION

This application is the national stage entry of International Patent Application No. PCT/KR2010/002360 having a filing date of Apr. 15, 2010, which claims priority to and the benefit of Korean Patent Application No. 10-2009-0040576 filed in the Korean Intellectual Property Office on May 11, 2009, Korean Patent Application No. 10-2009-0074234 filed in the Korean Intellectual Property Office on Aug. 12, 2009, and Korean Patent Application No. 10-2009-0074245 filed in the Korean Intellectual Property Office on Aug. 12, 2009, the entire contents of which are incorporated herein by reference.

BACKGROUND OF THE INVENTION (a) Field of the Invention

The present invention relates to a method of preparing bio fuel from algal galactan, and more particularly to a method of preparing bio fuel as an alternative to oil fuel, which has high energy density and low hygroscopic property, with a starting material of galactan easily derivable from macroalgae utilizable as marine biomass.

(b) Description of the Related Art

Currently, limited reserves of oil resources and appearance of a new developing country such as China or the like have caused an upsurge in oil prices due to increased demand, and the oil resources are on the brink of being exhausted in the foreseeable future. Further, the oil resources are nonrenewable so that the enormous environmental expenses can be expected based on the international covenant. Accordingly, all countries of the world have made a lot of effort to develop an alternative to the oil resources.

Carbohydrate-based biomass which can be recycled and sustainably used has been on the rise has emerged as the most realistic alternative to such irreversible fossil fuel. With the countries having a large arable land, e.g., the United States, Brazil, etc. as the center, sugar-based substance such as sugar cane or farinaceous-based substance such as corn is used as a starting material and undergoes saccharification and fermentation to industrially mass-produce bio ethanol. Thus, the bio ethanol is used for transportation fuel or the like.

The biomass is broadly divided into a crop system used as food like a sugar system (sugar cane, a sugar beet, etc.), a farinaceous system (corn, a potato, a sweat potato, etc.), and a lignocellulosic system (wood, rice straw, waste paper, etc.) Currently, a polysaccharide carbon source that can be got from the biomass may include starch or sugar got from a crop system supply resource, cellulose that can be got from the woody system supply source, etc. Such polysaccharide substance is got from a pretreatment of a biomass supply source, and the polysaccharide substance such as the starch, sugar and cellulose got from the pretreatment undergoes the saccharification based on hydrolysis and is converted into hexose such as glucose or fructose. Then, the hexose is converted into ethanol and butanol as petroleum-alternative fuel or an alternative material through bio-fermentation.

From the practical use point of the biomass resource, already-industrialized bio ethanol has so low energy content (e.g., about 75% of that gasoline has) that the existing engine has to be inevitably changed in order to use the bio ethanol as single fuel. Further, the bio ethanol is so highly hygroscopic that there is a high risk of corroding an engine or a pipe. Also, since 1/3 of a carbon source is emitted as carbon dioxide in light of material balance when glucose undergoes the bio-fermentation, it is fundamentally inefficient For the above reason, n-butanol has attracted attention as an alternative to ethanol. As compared with ethanol, n-butanol has high energy content and is lowly hygroscopic. However, new glucose fermentation is required, and researches for developing this are in progress.

To solve the foregoing problems, there is a furan-based compound such as 2,5-dimethylfuran (DMF) and 5-ethoxymethyl-2-furfural (EMF), called next-generation bio fuel that has attracted attention as another alternative using the carbohydrate-based biomass. Such a furan-based compound is excellent in energy content, is very lowly hygroscopic because of having no hydroxyl group as opposed to alcohols, and produces a little exhaust gas, thereby drawing interest.

Specifically, a general manufacturing method of deriving a desired final compound from a source of the carbohydrate-based biomass requires multistage processes of (a) the pretreatment for obtaining polysaccharide substance such as the starch, sugar and cellulose, (b) the saccharification for obtaining glucose or fructose, and (c) the bio-fermentation or catalysis-chemical process for obtaining the final compound. However, there is a problem of lowering a yield while experiencing the multistage processes.

Meanwhile, to employ the furan-based compound derived from the carbohydrate-based biomass as the petroleum-alternative fuel, a method of mass-producing a key intermediate platform material, 5-hydroxymethyl-2-furfural (HMF) shown in the following structural formulas has been being actively researched, in which HMF can be widely used as not only fuel materials but also a plastic monomer and an environment-friendly fine chemistry product such as an adhesive, a sticking agent, a coating material, etc. through various conversion reactions.

[Structural formulas]

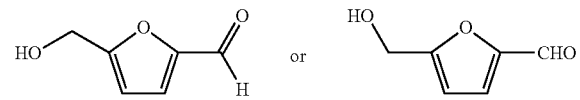

Hitherto, attempts to obtain HMF have been made by using the starting material of fructose mainly derived from the crop-based biomass supply source. This is because HMF can be relatively easily obtained from hexose such as fructose chemically having a pentagonal ring structure by only dehydration under an acid catalyst without separate isomerization.

[Reaction formulas of Dehydration of D-fructose]

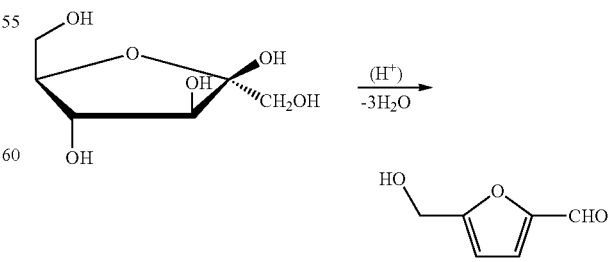

Representatively, the Dumesic group has made researches on enhancing a yield and selectivity by separating a product from reaction a mixture under a biphasic condition and thus developed technology of obtaining HMF with a conversion rate of 90% from fructose (Yuriy Roman-Leshkov, Juben N. Chheda, James A. Dumeic, Science, 2006, 312, 1933-1937). H. E. van Dam et al. has proposed a method of obtaining HMF from fructose using p-toluenesulfonic acid as a catalyst (H. E. van Dam, Dr. A. P. G. Kieboom, Prof. H. van Bekkum, Delft University of Technology, Laboratory of Organic Chemistry, Starch, 2006, Volume 38 Issue 3, Pages 95-101). Also, the Zhang group of PNNL has obtained HMF with a conversion rate of 83% from glucose using a chrome catalyst in ionic liquid, in which glucose more usually exists than fructose but has a low conversion rate because of chemically having a hexagonal ring structure (Haibo Zhao, Johnathan E. Holladay, Heather Brown, Z. Conrad Zhang, Science, 2007, 316, 1597-1600).

However, fructose, glucose or the like exists in only some limited supply sources such as sugar cane, corn, etc., or it is impossible to economically extract fructose, glucose or the like from such sources. Therefore, it is difficult to mass-produce fructose, glucose or the like. Like this, the bio fuel produced from the crop-based supply sources such as sugar cane, corn, etc. uses food resources and thus shares the arable land with the food resources, so that the international grain price can be raised and cropping costs tend to interlock with the oil prices, thereby entering into international dispute.

To solve these problems, interest in the lignocellulosic biomass is increasing since it uses lumber sharing no arable land with a crop, wood wastes from municipal wastes, or forestry byproducts scattering in everywhere of a forest as a raw material and can be massively supplied. However, in the case of the lignocellulosic biomass, it is difficult to efficiently separate and remove solid lignin occupying about 30% of the contents in the pretreatment, and there is a need of many researches on application of lignin wastes. Further, the starting material of the lignocellulosic biomass, i.e., cellulose is more physically and chemically stable than those of the crop-based biomass, i.e., starch or sugar, so that the conversion process thereof has a high level of difficulty.

Recently, Mascal et al. and Joseph et al. have succeeded in a reaction of converting 5-chloromethyl-2-furfural (CMF), i.e., a precursor of the next-generation fuel EMF from cellulose at a high yield of 75% or more, thereby increasing the possibility of massively producing EMF from the lignocellulosic biomass [Mascal, M.; Nikinin, E. B., Angew. Chem. Int. Ed. 2008, 47, 7924-7926; Joseph B. Binder et al., J. Am. Chem. Soc., 2009, 131(5), 1979-1985].

Nevertheless, hydrochloric acid having a devastating effect on an engine is produced as a byproduct in the process of etherealizing CMF, and is blocking the massive production.

To solve the above-mentioned problems, marine resources have come into the spotlight as the third-generation biomass. The marine resources such as marine algae or the like maritime plants have a large allowable aquaculture area, have little effect of advance on costs based on use of fresh water, a land, a fertilizer, etc., and have high production per unit area because their growth ability is higher than that of land plants. Also, the marine resources contain no irremovable ingredient such as lignin, thereby facilitating the pretreatment. Further, the marine resources are superior to the land plants with respect to $CO_2$ removal performance, thereby reducing greenhouse gas. Accordingly, development of conversion technology that produces bio fuel by employing marine biomass resources as a new supply source will be expected to carry an important meaning in an oil-free age.

Hitherto, the researches on the marine biomass have dealt mainly with a method of extracting triglycerides from microalgae and then converting it into fatty acid ester-based bio diesel through transesterification. However, it is hard to cultivate the microalgae in the maritime areas, and there is difficulty in a filtering process or the like.

SUMMARY OF THE INVENTION

According to an exemplary embodiment of the present invention, there is provided a method of preparing bio fuel by a single process without undergoing saccharification as an alternative to oil fuel from galactan derived from macroalgae biomass resources that enable economical massive cultivation, contain abundant carbohydrate-based carbon sources, and are easily extractable.

Accordingly, the present invention is conceived to solve the forgoing problems, and an aspect of the present invention is to provide a method of preparing bio fuel based on marine resources, in which galactan readily extractable as a chief ingredient of the marine algae is employed as a starting material, and which has higher energy density and lower hygroscopic property than gasoline, thereby replacing oil fuel or oil-based aromatic compounds.

Further, an exemplary embodiment of the present invention provides a method of producing bio fuel as an alternative to petroleum, using marine resources of macroalgae, as new biomass that can be massively cultivated without resource destruction or the like problem while having no effect on food resources as opposed to other biomass.

In the exemplary embodiments of the present invention, 'bio fuel,' the material derived from biomass, comprehensively refers to not only 'fuel' but also a 'petroleum-alternative material' that can replace any material produced from petroleum such as a plastic monomer, an adhesive, a sticking agent, a coating material, etc.

An exemplary embodiment of the present invention provides a method of preparing bio fuel from algal galactan, the method including preparing a starting material for extracting galactan as polysaccharide from marine algae (S10); and carrying out reaction for preparing bio fuel through a catalyst conversion reaction using the galactan (S20).

The bio fuel may include at least one of 5-hydroxymethyl-2-furfural (HMF) and 5-alkoxymethyl-2-furfural (AMF) represented by the following chemical formula I, and may further include levulinic acid alkyl ester represented by the chemical formula II.

[Chemical formula I]

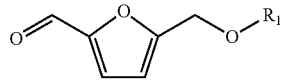

where, $R_1$ is one of hydrogen, alkyl, alkenyl, alkynyl, cycloalkyl and aryl groups.

[Chemical formula II]

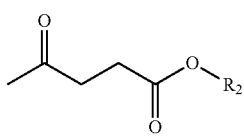

where, $R_2$ is one of alkyl, alkenyl, alkynyl, cycloalkyl and aryl groups.

For example, 5-hydroxymethyl-2-furfural (HMF) is when $R_1$ is hydrogen in the chemical formula I, and 5-alkoxymethyl-2-furfural (AMF) is when $R_1$ is one of alkyl, alkenyl, alkynyl, cycloalkyl and aryl groups.

As described above, as a representative key intermediate platform material that can be obtained from carbohydrate derived from renewable biomass, HMF is a material that can be widely used as not only a fuel material but also a bio-based plastic monomer as an alternative to an oil-based aromatic compound and a environment-friendly fine chemical product such as a sticking agent, a coating material, etc. through various conversion reactions. Meanwhile, AMF is known as an ether derivative and attracts attention as the next-generation fuel, energy density of which is equal to or higher than the conventional oil fuel such as gasoline, diesel, etc. and is far superior to bio-ethanol. Thus, as representative AMF, 5-methoxymethyl-2-furfural or 5-ethoxy-methyl-2-furfural may be used as an alternative to fossil fuel or additive agents for the fuel such as methyl tertiary butyl ether (MTBE) or the like.

The levulinic acid alkyl ester of the chemical formula II may be directly used for the bio fuel as an alternative to the fossil fuel, but may be employed as a noticeable starting material in preparing a plurality of useful 5-carbon compounds and its derivatives. For example, N-cyclohexyl-2-pyrrolidone prepared by the foregoing material may be employed as a solvent or an intermediate in a plurality of industrial applications such as electronic industry (photoresist stripping solution), an industrial cleaning agent, oil/gas well maintenance, fiber dyeing, etc. Also, N-[2-hydroxyethyl]-2-pyrrolidone is available in industrial cleaning, printing ink, and gasoline and oil additive agents. Further, N-octyl-2-pyrrolidone is useful as cleaning and dispersing agent in manufacturing an agricultural product, industrial metal cleaning agents, printing ink and fiber dyeing.

The preparation (S10) of the starting material simply refers to a step of extracting a polysaccharide material from marine algae. The reaction is carried out (S20) using galactan among such extracted polysaccharide materials, thereby obtaining bio fuel such as HMF, AMF, levulinic acid alkyl ester, etc. as an alternative to petroleum.

Here, the marine algae used in these exemplary embodiment includes macroalgae such as red algae, brown algae, green algae, etc. which live in the sea. The marine algae include anything without limitation as long as it contains galactan. As an example of red algae, there are agar-agar, layer, cottonni, *Pachymeniopsis lanceolate*, stone layer, *pterocladia tenuis*, *acanthopeltis*, *gloiopeltis*, *gracilaria*, *Chondrus ocellatus*, *Grateloupia elliptica*, *Hypnea*, *ceramium*, *Ceramium boydenii* Gepp, *Chondracanthus tenellus*, *Thiaspi arvense*, *Grateloupia imbricate*, etc. As an example of brown algae, there are seaweed, kelp, *Analipus japonicus*, *Chordaria flagelliformis*, *Ishige okamurae*, *scytosiphon lomentaria* (whip tube), *Endarachne binghamiae*, *Ecklonia cava*, *Ecklonia stolonifera*, *Eisenia bycyclis*, *Costaria costata*, *Sargassum fulvellum*, *Sargassum horneri*, *Sargassum thunbergii*, *Hizikia fusiformis*, etc. As an example of brown algae, there are green moss, spirogyra, green layer, *Codium fragile*, *Codium minus*, *Caulerpa okamurai*, *Chaetomorpha moniligera*, etc. From these marine algae, it is possible to polysaccharide such as cellulose, starch, etc. as well as galactan.

The method of deriving galactan from the marine algae may include any method without limitation as long as it is used in the relevant technical field. For example, the marine algae is soaked into alkali aqueous solution for a predetermined period of time and washed with water. Then, the washed marine algae is soaked into an extraction solvent containing acidic agents such as $H_2SO_4$, HCl, HBr, $HNO_3$, $CH_3COOH$, HCOOH, $HClO_4$ (perchloric acid), $H_3PO_4$, para-toluene sulfonic acid (PTSA), etc. for a predetermined period of time, thereby extracting agar, carrageenan, alginate ingredients The galactan used in these exemplary embodiments may include agar. As representative galactan, agar is a natural polymer containing agarose as a monomer, in which agarose is a disaccharide material consisting of galactose and 3,6-anhydrogalactose.

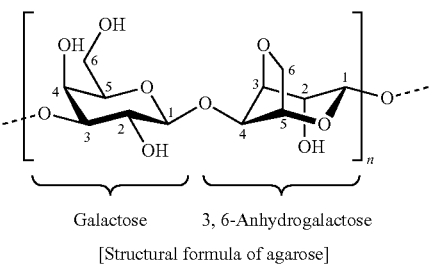

Galactose   3, 6-Anhydrogalactose

[Structural formula of agarose]

In light of chemical composition, it has been known that the amount of agar within galactan, which can be obtained from the macroalge through a simple pretreatment, reaches the maximum of about 50 to 60% of the total ingredients in the case of some red algae such as gelidium, gracilaria, etc. As the other chief ingredients, there are about 10 to 20% of glucan (cellulose), about 10 to 20% of protein, and about 5 to 15% of fatty or ash content, but these can be easily removed during the extraction or the like.

As opposed to cellulose having very low solubility due to a crystal form based on intramolecular hydrogen bonding, agar is an amorphous high-molecular substance having excellent solubility in a polar solvent. Specifically, agar can be dissolved in a hydrophilic organic solvent such as alcohol, water heated at about 80° C., etc. Such solubility is indispensable for an efficient chemical conversion reaction and thus very important. Further, like the reaction (S20) to be described later, if the conversion reaction is carried out based on a solid catalyst, such solubility offers an advantage that a heterogeneous solid acid catalyst or a metal catalyst can be employed. Here, the heterogeneous solid acid catalyst or the metal catalyst can be easily separated and refined, have no side reaction due to acid's counter-ions, be recycled, and be applied to successive processes.

According to an exemplary embodiment, the reaction (S20) is carried out to have the optimum condition for the conversion reaction, in which the catalyst containing one or both of the solid acid catalyst and the metal catalyst is added together with galactan into the solvent, thereby carrying out the catalyst conversion reaction.

That is, by the reaction (S20) carried out according to an exemplary embodiment, a single process is enough to obtain a target compound such as HMF, AMF or levulinic acid alkyl ester without converting polysaccharide galactan extracted in preparing the starting material (S10) into a monosaccharide through hydrolysis. The following reaction formula I schematically shows that the above compound is obtained by using agar as galactan through a single reaction.

[Reaction formula I]

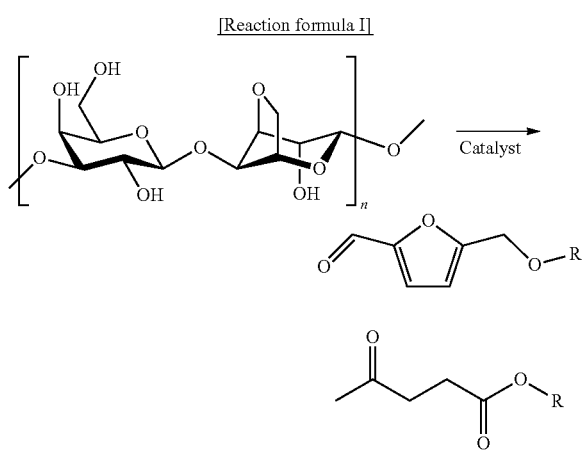

Referring to a mechanism of the catalyst conversion reaction used in this exemplary embodiment, it is as follows. First, if the solid acid catalyst is used, H+ is coupled to an oxygen atom in agar molecules and activated as a cation, thereby starting reaction while moving electrons in the agar molecules. At this time, chemical combination in the molecules is simultaneously broken or regenerated as the electrons move. Thus, a lot of intermediates having an equilibrium state exist in a reaction solution. As reaction time elapses, the equilibrium state is broken by dehydration, thereby carrying out conversion into a substance (HMF) having the most thermodynamically stable chemical structure. Further, if addition of an alcohol catalyst causes additional etherealization, 5-alkoxymethyl-2-furfural and levulinica alky ester are produced as a final product.

Here, what's interesting is that agar is more sensitively reacted under an acidic condition due to 3,6-anhydrogalactose having a large chemical-structural ring strain as opposed to cellulose, and agarose connection is not C1-C4 connection of general starch, cellulose or the like the crop-based biomass structure but C1-C3 connection. Therefore, it is expected that the intermediate of agar has a different chemical structure, and agar requires a new reaction condition such as the kind, strength and concentration of acidic catalyst or metal catalyst, the concentration of reaction solution, the kind of solvent, the temperature, time, etc., entirely different from that of glucose, fructose and cellulose which are the starting material for deriving the existing crop and lignocellulosic biomass resources.

As the catalyst used in this exemplary embodiment, not only general organic/inorganic acid catalysts such as formic acid, acetic acid, trifluoroacetic acid (TFA), sulphuric acid, nitric acid, hydrochloric acid, phosphoric acid, etc. but also one of the solid acid catalyst and the metal catalyst or a mixture of them may be used.

The (heterogeneous) solid acid catalyst may include various ion exchange resins, zeolite, metal silicate, acid resins, natural clay minerals, silica impregnated with mineral acid, heat-treated charcoal, metal oxide, metal sulfide, metallic salts, mixed oxide, or a mixture of them, but not limited thereto. In the present exemplary embodiment, the solid Brønsted acid catalyst will be used in the form of a cation exchange resin as the solid acid catalyst.

Without limitation, the metal catalyst may include any material that can be represented by MXn or MXn.H$_2$O, in which M is a metallic element, X is a halogen element or a functional group including or corresponding to the halogen element, and n is 1 to 3. For example, the halogen element includes Cl, Br, I, etc. and the functional group including or corresponding to the halogen element includes triflate, nonaflate, mesylate, ethylsulfonate, benzenesulfonate, tosylate, triisopropyl-benzenesulfonate, formate, acetate, trifluoroacetate, nitro-benzoate, and halogenated aryl carboxylate, and particularly includes one of fluoro benzoate, methyl carbonate, ethyl carbonate, benzyl carbonate, t-butyl carbonate, dimethyl phosphonate, diphenyl phosphonate, and diazonium or diazonium. Among them, the halogen element and one of the functional groups such as triflate, nonaflate, mesylate, tosylate or diazonium may be used.

Here, the metallic element may be selected from a group consisting of Mn, Ni, Fe, Cr, Cu, Co, Ru, Zn, Al, Ce, La, Nd, Sc, Yb and In.

Also, as an example of the metal catalyst, there may be used a heterogeneous metal catalyst that can be represented by the following chemical formula III, and include a solid imidazole ligand consisting of a high molecular resin and an imidazole compound, in which a metallic element is coordinated to the imidazole ligand.

[Chemical formula III]

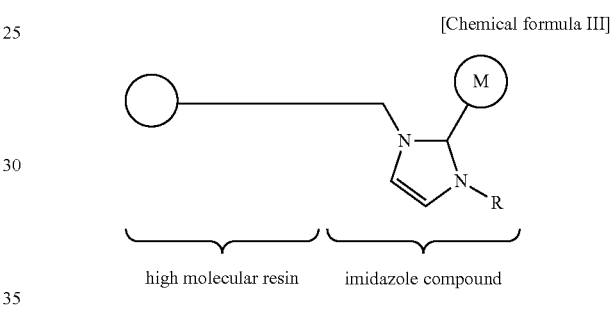

where, R is an alkyl or methyl group that contains or does not contain a hetero atom, and M is a metallic element.

With this configuration, the heterogeneous metal catalyst according to an exemplary embodiment, an imidazole compound such as N-methylimidazole or the like known as a ligand of the metallic element to increase the activity of the catalyst is introduced to a bead made of a high molecular resin through a covalent bond by a solid organic synthesizing reaction, and then the metallic element is coordinated to the imidazole ligand, thereby converting the conventional ionic liquid imidazole compound into a solid state. After the reaction is completed, the heterogeneous catalyst is formed to be easily separated and refined, and catalyst activity is improved.

Specifically, if polystyrene is used as the high molecular resin and methylimidazole is used as the imidazole compound connected to the high molecular resin although it is not limited thereto, the heterogeneous catalyst has a structure as shown in the following chemical formula IV.

[Chemical formula IV]

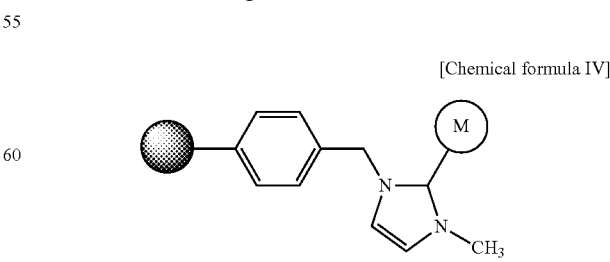

Also, the metallic element is selected from a group consisting of transition metal, alkali metal, lanthanide metal, and mercury (Hg). Specifically, the transition metal includes one of Cr, Mn, Fe, Co, Ni, Cu, Zn, Au, Ru, Rh and Pt. The alkali metal includes Li or Rb. The lanthanide metal includes one of La, Ce and Nd. Besides the foregoing metallic elements, Lewis's acid such as $AlCl_3$, etc. or sulfuric acid or the like may be used.

If the heterogeneous metal catalyst proposed in the chemical formula IV is used, the conventional process of separating and refining the final product due to use of a homogeneous catalyst is not needed, and an economic problem for scale-up due to use of an expensive substance such as ionic liquid. That is, the use of the heterogeneous metal catalyst offers advantages that the final product can be easily separated and refined and a target furan compound can be efficiently obtained at a high yield without using the expensive substances.

Also, the solvent includes one or a mixture of alcohol, ionic liquid and an aprotic polar solvents.

The alcohol solvent used in this exemplary embodiment may include methanol, ethanol, propanol, 2-hydroxymethyl-propanol, butanol, etc. as a primary aliphatic alcohol. The ionic liquid may include one or a mixture of ethylmethylimidazolium chloride [EMIM]Cl, ethylmethylimidazolium bromine [EMIM]Br, ethylmethylimidazolium iodine [EMIM]I, etc. The aprotic polar solvent may include one or a mixture of dimethylacetamide (DMA), dimethyl sulfoxide (DMSO), dimethylformamide (DMF), hexamethylphosphortriamide, N-methylpyrrolidone, tetrahydrofuran (THF), γ-butyrolactone, etc. The alcohol solvent is used to have a reaction for producing AMF and levulinic alkyl ester particularly used as the 'alternative fuel' among the bio fuel, and the ionic liquid and/or aprotic polar solvent is used to have a reaction for preparing the alternative fuel like the alcohol solvent or producing HMF.

Here, a ratio of galactan to the solvent may range from 0.5 to 50 g/L, and more specifically range from 1 to 20 g/L (wt/V). This ratio showed the excellent yield. Also, the concentration of the solid acid catalyst for maximizing the yield may range from 0.05 to 1.0M, and more specifically range from 0.1 to 0.5M. Also, the equivalent of the metal catalyst may range from 0.05 to 50 mol %, and more specifically range from 0.1 to 20 mol %. Further, the temperature of carrying out the reaction (S20) according to an exemplary embodiment may range from 50 to 200° C., and more specifically range from 70 to 150° C., and the reaction time thereof may range from 1 to 50 hours, and more specifically range from 2 to 20 hours. In general, if the temperature is lower than 50° C., the reaction is not carried out well, and if the temperature is higher than 200° C., a lot of humin and the like byproducts are produced to thereby decrease a yield.

Thus, a method of preparing bio fuel from algal galactan according to an exemplary embodiment can simply prepare bio fuel through a single process without saccharification.

BRIEF DESCRIPTION OF THE DRAWINGS

The above and/or other aspects of the present invention will become apparent and more readily appreciated from the following description of the exemplary embodiments, taken in conjunction with the accompanying drawings, in which.

DETAILED DESCRIPTION OF THE EMBODIMENTS

Hereinafter, exemplary embodiments will be described with reference to accompanying drawings.

In the following exemplary embodiments, agar as biomass derived from marine resources and HMF produced by a solid acid catalyst reaction using land crop-based biomass are compared and examined with respect to a yield.

The solid acid catalyst reaction is as shown in the following reaction formula II.

[Reaction formula II]

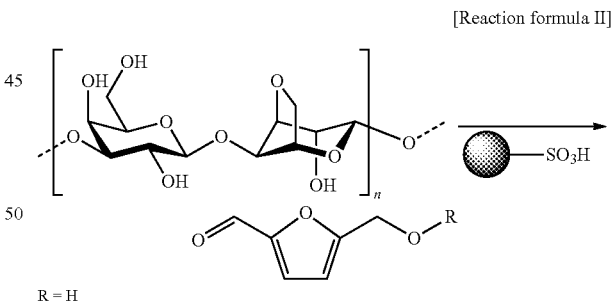

R = H

Exemplary Embodiment 1

Direct Conversion into HMF from Agar that is Carbohydrate Derived from Red Macroalgae with a Solid Brønsted Acid Catalyst and a Solid Catalyst Exemplary Embodiment 1-1

In a 6 mL-Vial, 200 mg of agar (prepared by Junsei chemicals Co., Ltd) extracted from red algae was used as a substrate, 50 wt % (100 mg) of Dowex 50WX8-200 ion exchange resin (prepared by Sigma-Aldrich Co., Ltd, hereinafter referred to as 'Dowex') was used as a solid acid catalyst, and DMSO (prepared by Samchun chemical Co., Ltd, solvent/substrate=10 wt %, i.e., 2 mL DMSO) was used as a solvent. The reaction was carried out by magnetic stirring (320 rpm) for 5 hours at 110° C. After the reaction, it is cooled up to room temperature, and resin and infusible ingredients were filtered off.

Comparative Example 1-1

The same reaction as the exemplary embodiment 1-1 was carried out except that the same amount (200 mg) of starch and cellulose of a polysaccharide, i.e., the lad crop-derived biomass were used as a substrate instead of agar, and aldose-type glucose and galactose were used as a monosaccharide.

Exemplary Embodiment 1-2

The same reaction as the exemplary embodiment 1-1 was carried out except that 5 wt % metal catalyst $CrCl_2$ was further added to the substrate.

Comparative Example 1-2

The same reaction as the comparative example 1-1 was carried out except that 5 wt % metal catalyst $CrCl_2$ was further added to the substrate.

Results

Figure 1:
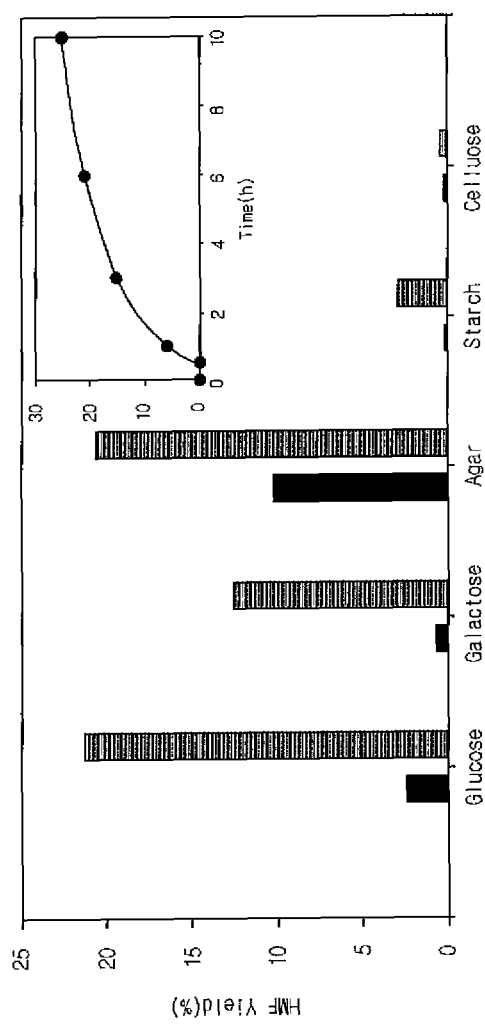
FIG. 1 is a graph showing HMF yields based on exemplary inventive embodiments 1-1 and 1-2 and comparative examples 1-1 and 1-2, in which left bars (dark color) between two bars on respective biomasses are related to the exemplary embodiment 1-1 and the comparative example 1-1 (results from reaction without a metal catalyst), and right bars (bright color) are related to the exemplary embodiment 1-2 and the comparative example 1-2 (results from reaction with a metal catalyst), and also a graph in a right topside box of FIG. 1 shows an HMF yield distribution curve based on time in accordance with the exemplary embodiment 1-1.

FIG. 1 is a graph showing HMF yields based on exemplary inventive embodiments 1-1 and 1-2 and comparative examples 1-1 and 1-2, in which the yield is derived as the weight of a product against the weight of a reactant.

Regarding the respective biomass (glucose, galactose, agar, starch and cellulose), the left bars show results from the exemplary embodiment 1-1 and the comparative example 1-1 (using only the solid acid catalyst (Solid Brønsted acid catalyst)), and the right bars show results from the exemplary embodiment 1-2 and the comparative example 1-2 (using combination of the solid acid catalyst and the metal catalyst).

As shown in the left bars of the respective items (the exemplary embodiment 1-1 and the comparative example 1-1), the yields of HMF produced from glucose and galactose through the catalyst reaction using only the solid acid catalyst are 2.3% and 0.6%, respectively. Further, there was little conversion from cellulose and starch into HMF. On the other hand, the yield of HMF produced from agar through the catalyst reaction was as high as 10%.

Thus, under the condition of the comparative example 1-1, an isomerization reaction from C1-aldose into C2-ketose does not occur, and it is regarded that cellulose is not dissolved in DMSO.

What's interesting was that in the case of agar, HMF was produced at a yield (about 21%) 16 times higher than that of glucose, i.e., the monosaccharide contained in agar. As described above, this may be because reactivity under an acid environment becomes higher due to 3,6-anhydrogalactose having a large chemical-structural ring strain, and a unit of a C1-C3 connection structure is repeated.

Also, as shown in the right bars of the respective items (the exemplary embodiment 1-2 and the comparative example 1-2), if the metal catalyst ($CrCl_2$) is additionally applied to glucose and galactose, HMF was produced at 10 to 20 times higher yields (21% and 12%) than that of when the metal catalyst is not used.

$CrCl_2$ accelerates isomerization from aldose into ketose, which forms furanose so that a hemiacetal part of aldose can be organized to provide HMF [Zhao, H.; Holladay, J. E.; Brown, H.; Zhang, Z. C., Science, 2007, 316, 1579-1600.]

In the case of agar having a yield of 21%, the yield was improved, but its effect was not significant as compared with those of glucose and galactose. This is a clue that agar is converted into HMF via another type of intermediate.

Referring to the reaction progress shown in the right topside box of FIG. 1, no reaction occurs for 0.5 hours, and then HMF falls being produced. For 10 hours, the yield of HMF increases up to 25%.

Exemplary Embodiment 2

Figure 2:
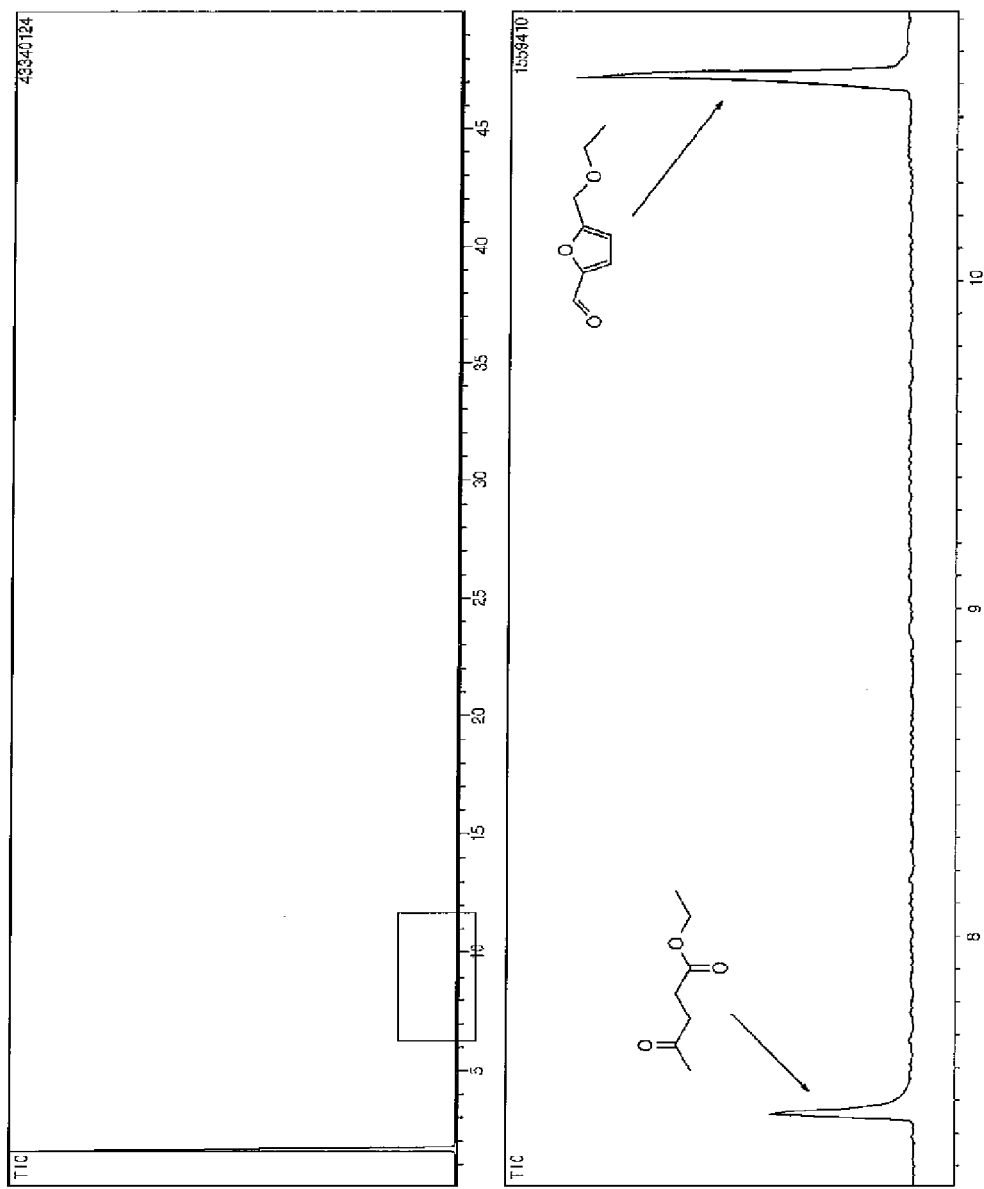
FIG. 2 is a graph showing a GC-MS chromatogram of crude produced by an exemplary embodiment 2, in which respective peaks indicate EMF (right) and LAFE (left)
Figure 3:
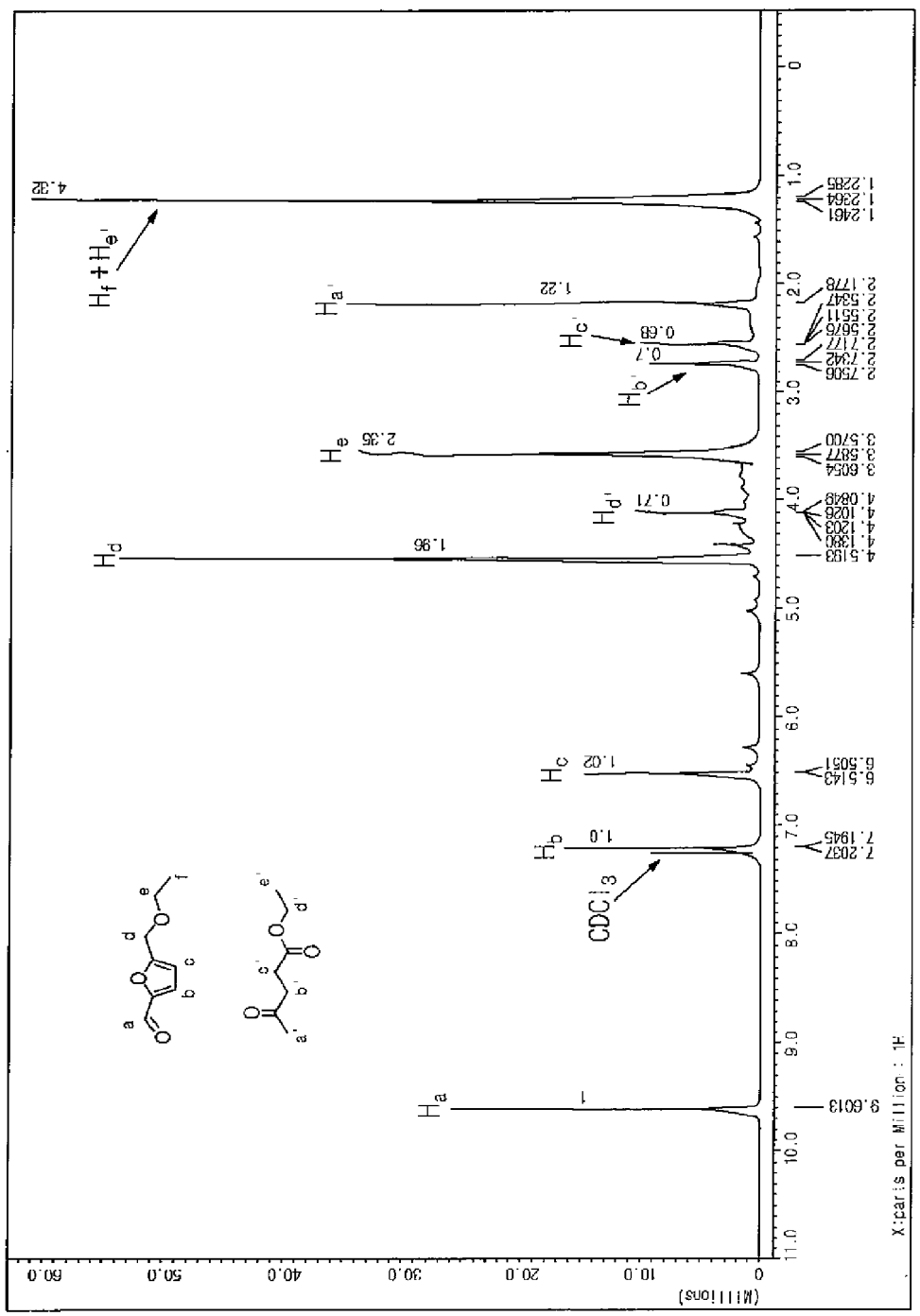
FIG. 3 is a graph showing $^1H$ FT-NMR of crude produced by the exemplary embodiment 2.

Direct Conversion into Alternative Fuel from Agar that is Carbohydrate Derived from Red Macroalgae with a Solid Brønsted Acid Catalyst and a Solid Catalyst 5 g of ethylmethylimidazolium chloride [EMIM]Cl (prepared by Sigma-Aldrich Co. Ltd.) and 500 mg of $CrCl_2$ (5 wt % of the substrate) were put into a 500 mL round bottom flask, and heated up to 90° C. The above mixture was cooled at room temperature for 10 minutes. 50 ml of ethanol (prepared by Sigma-Aldrich Co. Ltd.) and 5 g (dry weight) of activated Dowex resin were added into the mixture, and then 50 ml ethanol and 10 g of agar as the substrate were added again and underwent magnetic stirring. The reaction was carried out at 90° C. for 15 hours. After the reaction is completed, ethanol was evaporated under a decompression condition (about 15 Torr). Residues were dissolved in DCM, and 3 times cleaned with salt water. An organic layer was separated and dried into $MgSO_4$, and DCM was evaporated to get a brownish liquid (3.9 g). The crude was analyzed by GC-MS (see FIG. 2) and $^1$H FT-NMR (see FIG. 3), and it was thus ascertained that 5-ethoxymethyl-2-furfural (EMF) and levulinic acid butyl ester (LAEE) were produced at a ratio of 5:2 (EMF:LAFE=5:2).

Then, this is separated by chromatography (silica, $CH_2Cl_2$: $Et_2O$=2:1) and refined, and therefore a yellow mixture solution of EMF and LAEE was produced at a yield of 30% wt/wt (3 g). EMF: $^1$H NMR (400 MHz, $CDCl_3$) δ 9.61 (s, 1H), 7.21 (d, 1H, J=3.4 Hz), 6.52 (d, 1H, J=3.2 Hz), 4.53 (s, 2H), 3.59 (q, 2H, J=7.0 Hz), 1.23 (t, 3H, J=6.9 Hz) $^{13}$C NMR (100 MHz, $CDCl_3$) δ 178.1, 159.1, 152.9, 122.3, 111.3, 67.0, 65.0, 15.4. LAEE: $^1$H NMR (400 MHz, $CDCl_3$) δ 4.12 (q, 2H, J=7.2 Hz), 2.74 (t, 2H, J=6.8 Hz), 2.59 (t, 2H, J=6.8 Hz), 2.19 (s, 3H), 1.24 (t, 3H, J=7.1 Hz) $^{13}$C NMR (100 MHz, $CDCl_3$) δ 207.1, 173.1, 61.0, 38.2, 30.2, 28.3, 14.5.

The above catalyst reaction is as shown in the following reaction formula III.

[Reaction formula III]

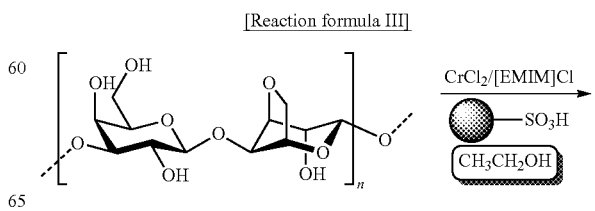

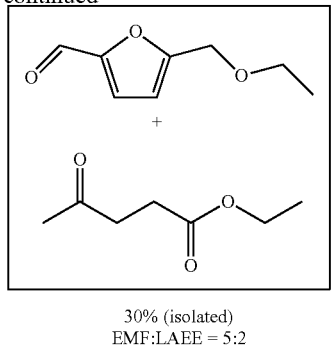

30% (isolated)
EMF:LAEE = 5:2

Hereinbelow, a method of preparing HMF and alternative fuel using galactan derived from marine algae will be described according to exemplary embodiments.

Exemplary Embodiment 3

HMF Prepared Using a Metal Catalyst (Examination of Yields Depending on the Kinds of Metal Catalyst)

Exemplary Embodiment 3-1

Figure 4:
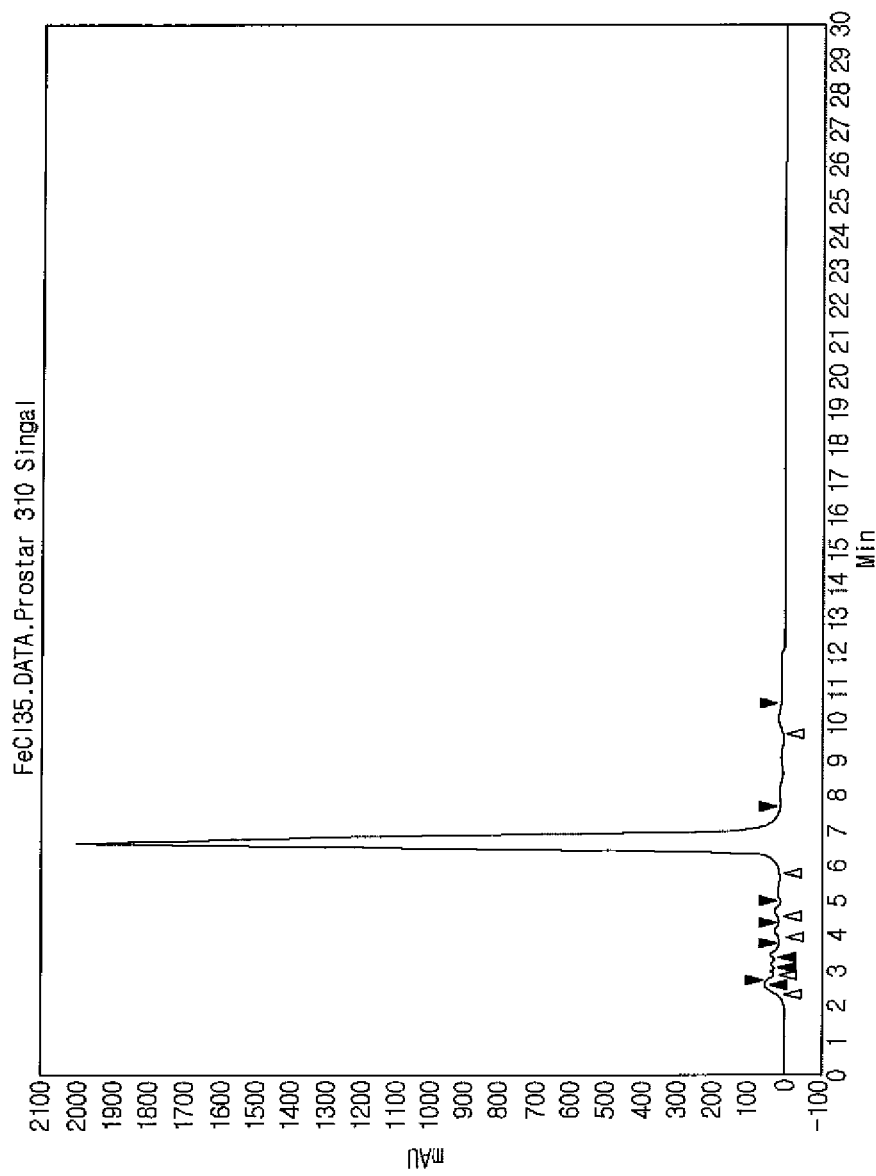
FIG. 4 is a view showing an HPLC chromatogram of HMF produced from agar through an exemplary embodiment 3-1 (metal catalyst: $FeCl_3$, temperature: 90° C., and reaction time: 2 h)

50 mg of agar, 500 mg of ethylmethylimidazolium chloride [EMIM]Cl as an ionic liquid solvent and 10 mol % of each of 13 metal catalysts shown in the following table 1 were put into a 5 mL-vial, and they were slowly heated up to 90° C. and then reacted for 2 hours while being stirred. After the reaction, a solid material based on a side reaction in a reaction mixture, i.e., humin was filtered off and the mixture was diluted. Then, the yields of HMF produced through HPLC were measured and tabulated in the table 1. Also, as shown in FIG. 4, this showed that 95% or higher pure HMF exists on a HPLC UV detector (283 nm).

TABLE 1

Yields of HMF produced depending on metal catalysts (at 90° C.)

| No. | Metal catalyst | Solvent | temperature (° C.) | time (h) | yield (g/L) |
|---|---|---|---|---|---|
| 1 | $FeCl_3$ | [EMIM]Cl | 90 | 2 | 3.3 |
| 2 | $CuCl_2$ | [EMIM]Cl | 90 | 2 | 3.0 |
| 3 | $NiCl_2$ | [EMIM]Cl | 90 | 2 | 0.3 |
| 4 | $CoCl_2\ 6H_2O$ | [EMIM]Cl | 90 | 2 | 0.2 |
| 5 | $CrCl_2$ | [EMIM]Cl | 90 | 2 | 0.1 |
| 6 | $ZnCl_2$ | [EMIM]Cl | 90 | 2 | 0.1 |
| 7 | $MnCl_2$ | [EMIM]Cl | 90 | 2 | 0.1 |
| 8 | $FeCl_2$ | [EMIM]Cl | 90 | 2 | 0.0 |
| 9 | $RuCl_3$ | [EMIM]Cl | 90 | 2 | 6.4 |
| 10 | $FeBr_3$ | [EMIM]Cl | 90 | 2 | 4.3 |
| 11 | $CuBr_2$ | [EMIM]Cl | 90 | 2 | 4.3 |
| 12 | $AlCl_3$ | [EMIM]Cl | 90 | 2 | 3.6 |
| 13 | $AlBr_3$ | [EMIM]Cl | 90 | 2 | 1.7 |

Exemplary Embodiment 3-2

50 mg of agar, 500 mg of ethylmethylimidazolium chloride [EMIM]Cl as an ionic liquid solvent and 10 mol % of each of 8 metal catalysts shown in the following table 2 were put into a 5 mL-vial, and they were slowly heated up to 110° C. and then reacted for 2 hours while being stirred. After the reaction, a solid material based on a side reaction in a reaction mixture, i.e., humin was filtered off and the mixture was diluted. Then, the yields of HMF produced through HPLC were measured and tabulated in the table 2.

TABLE 2

Yields of HMF produced depending on metal catalysts (at 110° C.)

| No. | Metal catalyst | Solvent | temperature (° C.) | time (h) | yield (g/L) |
|---|---|---|---|---|---|
| 1 | $CrCl_2$ | [EMIM]Cl | 110 | 2 | 6.1 |
| 2 | $MnCl_2$ | [EMIM]Cl | 110 | 2 | 5.1 |
| 3 | $NiCl_2$ | [EMIM]Cl | 110 | 2 | 5.0 |
| 4 | $CoCl_2\ 6H_2O$ | [EMIM]Cl | 110 | 2 | 4.5 |
| 5 | $FeCl_2$ | [EMIM]Cl | 110 | 2 | 4.5 |
| 6 | $ZnCl_2$ | [EMIM]Cl | 110 | 2 | 4.4 |
| 7 | $FeCl_3$ | [EMIM]Cl | 110 | 2 | 0.9 |
| 8 | $CuCl_2$ | [EMIM]Cl | 110 | 2 | 0.7 |

Exemplary Embodiment 3-3

50 mg of agar, 0.5 mL of ethylmethylimidazolium chloride [EMIM]Cl as an ionic liquid solvent and 10 mol % of each of 7 metal catalysts shown in the following table 3 were put into a 5 mL-vial, and they were slowly heated up to 80° C. and then reacted for 5 hours and 20 hours while being stirred. After the reaction, a solid material based on a side reaction in a reaction mixture, i.e., humin was filtered off and the mixture was diluted. Then, the yields of HMF produced through HPLC were measured and tabulated in the table 3.

TABLE 3

Yields of HMF produced depending on metal catalysts (at 80° C.)

| No. | Metal catalyst | Solvent | temperature (° C.) | time (h) | yield (g/L) |
|---|---|---|---|---|---|
| 1 | $CuCl_2$ | [EMIM]Cl | 80 | 20 | 2.0 |
| 2 | $FeCl_3$ | [EMIM]Cl | 80 | 20 | 1.9 |
| 3 | $FeCl_3$ | [EMIM]Cl | 80 | 5 | 0.8 |
| 4 | $CuCl_2$ | [EMIM]Cl | 80 | 5 | 0.0 |

Exemplary Embodiment 3-4

50 mg of agar, 500 mg of ethylmethylimidazolium bromide [EMIM]Br as an ionic liquid solvent and 10 mol % of each of 12 metal catalysts shown in the following table 4 were put into a 5 mL-vial, and they were slowly heated up to 90° C. and then reacted for 2 hours while being stirred. After the reaction, a solid material based on a side reaction in a reaction mixture, i.e., humin was filtered off and the mixture was diluted. Then, the yields of HMF produced through HPLC were measured and tabulated in the table 4.

TABLE 4

Yields of HMF produced depending on metal catalysts (with the solvent of [EMIM]Br)

| No. | Metal catalyst | Solvent | temperature (° C.) | time (h) | yield (g/L) |
|---|---|---|---|---|---|
| 1 | $RuCl_3$ | [EMIM]Br | 90 | 2 | 2.6 |
| 2 | $FeCl_3$ | [EMIM]Br | 90 | 2 | 1.0 |
| 3 | $CuCl_2$ | [EMIM]Br | 90 | 2 | 0.9 |
| 4 | $CuBr_2$ | [EMIM]Br | 90 | 2 | 0.4 |
| 5 | $AlCl_3$ | [EMIM]Br | 90 | 2 | 0.2 |
| 6 | $CoCl_2\ 6H_2O$ | [EMIM]Br | 90 | 2 | <0.1 |
| 7 | $FeCl_2$ | [EMIM]Br | 90 | 2 | <0.1 |
| 8 | $MnCl_2$ | [EMIM]Br | 90 | 2 | <0.1 |
| 9 | $NiCl_2$ | [EMIM]Br | 90 | 2 | <0.1 |
| 10 | $ZnCl_2$ | [EMIM]Br | 90 | 2 | <0.1 |
| 11 | $AlBr_3$ | [EMIM]Br | 90 | 2 | <0.1 |
| 12 | $FeBr_3$ | [EMIM]Br | 90 | 2 | <0.1 |

Exemplary Embodiment 3-5

50 mg of agar, 0.5 mL of DMSO as a solvent, and 10 mol % of each of 4 metal catalysts shown in the following table 5 were put into a 5 mL-vial, and they were slowly heated up to 90° C. and then reacted for 2 hours while being stirred. After the reaction, a solid material based on a side reaction in a reaction mixture, i.e., humin was filtered off and the mixture was diluted. Then, the yields of HMF produced through HPLC were measured and tabulated in the table 5.

TABLE 5

Yields of HMF produced depending on metal catalysts (with the solvent of DMSO)

| No. | Metal catalyst | Solvent | temperature (° C.) | time (h) | yield (g/L) |
|---|---|---|---|---|---|
| 1 | $RuCl_3$ | DMSO | 90 | 2 | 3.6 |
| 2 | $CrCl_2$ | DMSO | 90 | 2 | <0.1 |
| 3 | $FeCl_3$ | DMSO | 90 | 2 | <0.1 |
| 4 | $CuCl_2$ | DMSO | 90 | 2 | <0.1 |

Exemplary Embodiment 3-6

50 mg of agar, 0.5 mL of ethylmethylimidazolium chloride [EMIM]Cl as an ionic liquid solvent and 10 mol % of each of 7 metal catalysts shown in the following table 6 were put into a 5 mL-vial, and they were slowly heated up to 90° C. and then reacted for 2 hours while being stirred. After the reaction, a solid material based on a side reaction in a reaction mixture, i.e., humin was filtered off and the mixture was diluted. Then, the yields of HMF produced through HPLC were measured and tabulated in the table 6.

TABLE 6

Yields of HMF produced depending on metal catalysts

| No. | Metal catalyst | Solvent | temperature (° C.) | time (h) | yield (g/L) |
|---|---|---|---|---|---|
| 1 | $BiCl_3$ | [EMIM]Cl | 90 | 2 | <0.1 |
| 2 | $CeCl_3\, 7H_2O$ | [EMIM]Cl | 90 | 2 | <0.1 |
| 3 | $InCl_3$ | [EMIM]Cl | 90 | 2 | <0.1 |
| 4 | $LaCl_3\, 7H_2O$ | [EMIM]Cl | 90 | 2 | <0.1 |
| 5 | $NdCl_3\, 6H_2O$ | [EMIM]Cl | 90 | 2 | <0.1 |
| 6 | $Sc(OTf)_3$ | [EMIM]Cl | 90 | 2 | <0.1 |
| 7 | $Yb(OTf)_3$ | [EMIM]Cl | 90 | 2 | <0.1 |

The exemplary embodiments 3-1 to 3-3 showed that the yields of HMF conversion with $FeCl_3$, $RuCl_3$, $FeBr_3$, $CuBr_3$ were excellent when the reactions were made on ionic liquid ethylmethylimidazolium chloride [EMIM]Cl with various metal catalysts at 90° C. for 2 hours. Curiously, under some conditions, $CrCl_2$ conventionally known as the excellent catalyst on the HMF conversion of glucose did not have a great effect on the case of agar. As described in the above exemplary embodiment 3-1, it is known that isomerization is required in order to convert a hexagonal ring structural compound such as glucose into a pentagonal ring structural HM, and Cr plays the role for the isomerization. However, in the case of agar, an intermediate thereof was expected to have a new chemical structure due to its unique chemical structure, and thus metal catalysts such as Fe and Ru other than Cr were more effective in the HMF conversion under some conditions. However, as shown in the exemplary embodiments 3-2, Cr had the highest activity when the reaction temperature is raised up to 110° C. This may be because the dehydration is promoted at 110° C. higher than the boiling point of water and galactose having a similar chemical structure similar to glucose is primarily produced from agar so that HMF can be produced by the same mechanism as glucose. Further, in the case of using the metal catalyst together with the solid acid catalyst, $CrCl_2$ had an excellent effect as shown in the exemplary embodiment 1.

Meanwhile, as results of replacing the solvent with [EMIM]Br (exemplary embodiment 3-4) or DMSO (exemplary embodiment 3-5), $RuCl_3$ and $FeCl_3$ showed the best performance as described above, but the yields thereof were decreased. Also, as shown in the exemplary embodiment 3-6, the HMF conversion rarely progressed with the metal catalysts promoting good dehydration, such as $BiCl_3$, $InCl_3$, $LaCl_3\, 7H_2O$, $NdCl_3\, 6H_2O$, $Sc(OTf)_3$, $Yb(OTf)_3$.

Next, a method of preparing alternative fuel using a solid acid catalyst will be described. The exemplary embodiment 2 showed the examples where both the solid acid catalyst and the metal catalysts are used, but the following exemplary embodiment 4 will show a method of preparing the alternative fuel using only the solid acid catalyst.

Exemplary Embodiment 4

Alternative Fuel Produced Using Only a Solid Acid Catalyst

Exemplary Embodiment 4-1

Production of 5-ethoxymethyl-2-furfural (EMF), and Levulinic Acid Ethyl Ester (LAEE)

1 g of agar, 1 g of Dowex ion exchange resin as a solid acid catalyst, and 20 mL of n-ethanol as a solvent and a reagent were put into a 250 mL round bottom flask and stirred to make suspension. Further, a reflux condenser was installed and temperature was slowly raised up to 80° C. Then, the suspension was stirred at 240 rpm, and reacted for 18 hours. At this time, colorless solution was changed to be brown (when about 4 to 5 hours elapse after the reaction initiation). The solution was separated and underwent HPLC (see FIG. 5) and GC-Mass analysis, and it was thus ascertained that a ratio of 5-ethoxymethyl-2-furfural and levulinic acid ethyl ester is 3:1 (selectivity>90%). After the reaction, a solid acid catalyst and a solid material based on a side reaction in a reaction mixture, i.e., humin ware filtered off, and a mixture produced by removing the solvent of the remaining solution under decompression was separated by the column chromatography (hexane:ethyl acetate=10:1→5:1) to thereby produce a mixture of 5-ethoxymethyl-2-furfural and levulinic acid ethyl ester at a yield of 10% (100 mg), which was ascertained through NMR (see FIG. 6).

Figure 5:
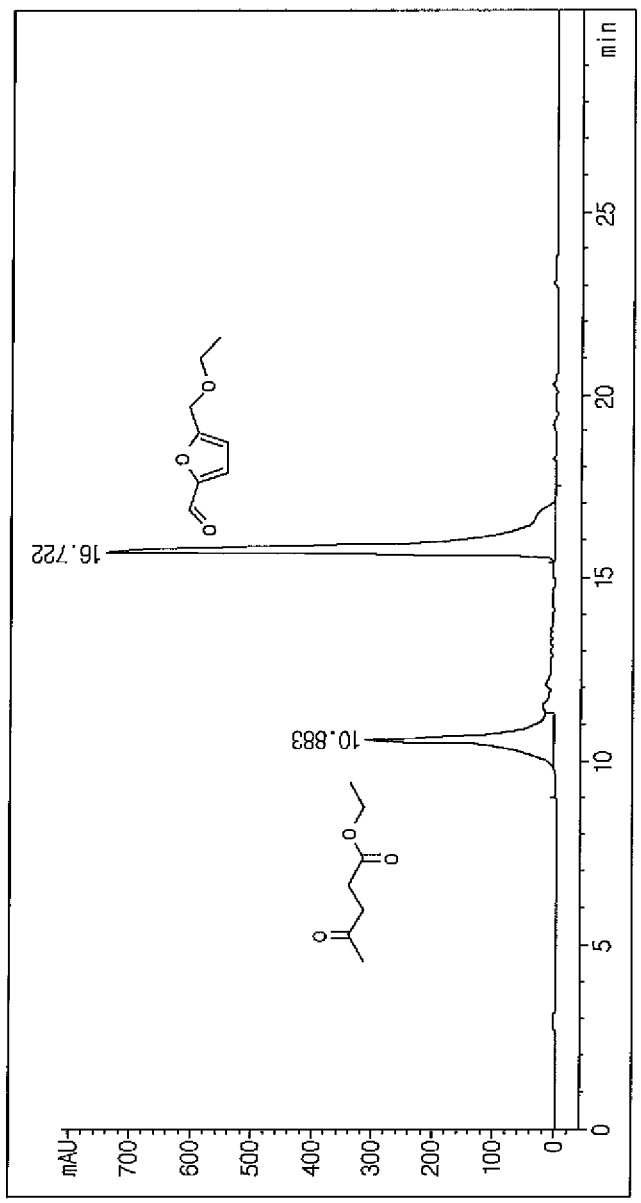
FIG. 5 is a view showing HPLC of a product material according to an exemplary embodiment 4-1, in which peaks indicate EMF and LAFE, respectively.

FIG. 5 is a view showing HPLC of a material produced from agar through a solid acid catalyst conversion process with the ethanol solvent, in which peaks indicate 5-ethoxymethyl-2-furfural and levulinic acid ethyl ester, respectively.

Figure 6:
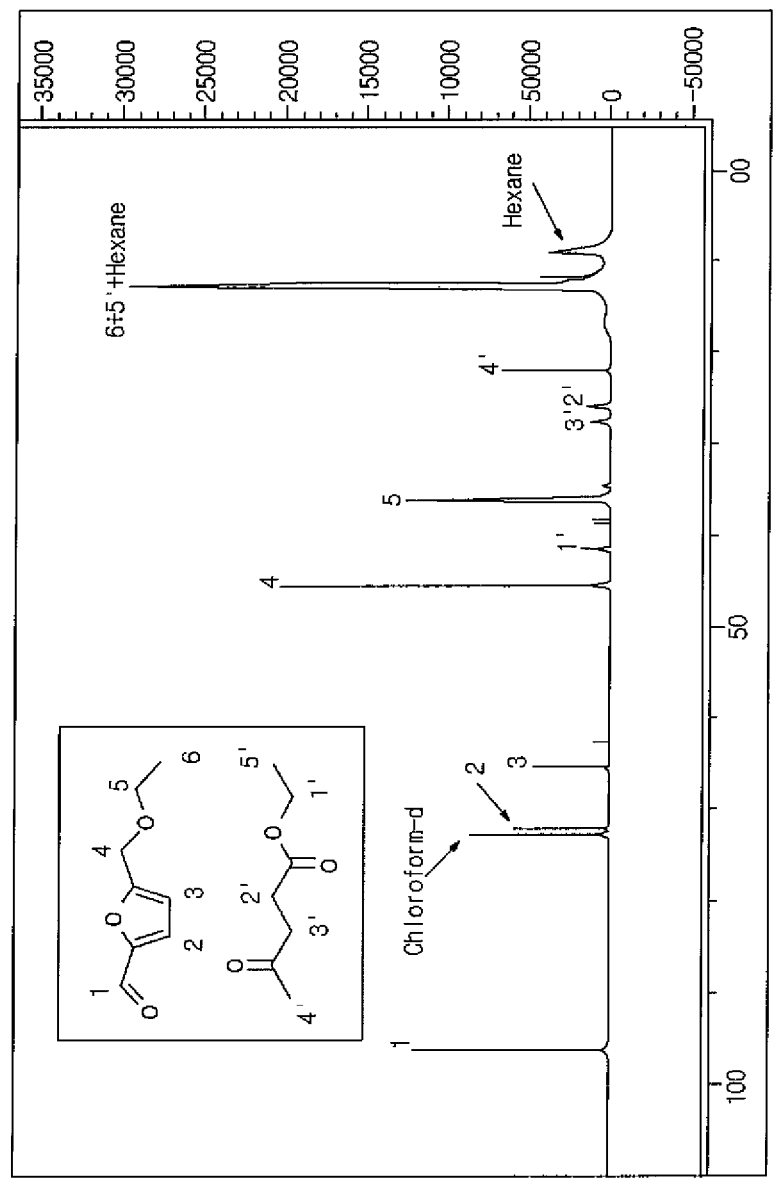
FIG. 6 is a view showing $^1H$-NMR of a mixture between EMF and LAFE obtained after being separated and refined by applying column chromatography to a product material according to an exemplary embodiment 4-1, in which location of a proton corresponding to each material is represented as a numeral.

Also, FIG. 6 is a view showing $^1H$-NMR of a mixture between 5-ethoxymethyl-2-furfural and levulinic acid ethyl ester, obtained after a material produced from agar is separated and refined by the column chromatography, in which location of a proton corresponding to each material is represented with a numeral.

Exemplary Embodiment 4-2

Production of 5-butoxymethyl-2-furfural and Levulinic Acid Butyl Ester, with 5% Agar Solution 1 g of agar, 1 g of Dowex ion exchange resin as a solid acid catalyst, and 20 mL of n-butanol as a solvent and a reagent were put into a 250 mL round bottom flask and stirred to make suspension. Further, a reflux condenser was installed and temperature was slowly raised up to 90° C. Then, the suspension was stirred at 240 rpm, and reacted for 30 hours. At this time, colorless solution was changed to be brown (when about 4 to 5 hours elapse after the reaction initiation). After the reaction, a solid acid catalyst and a solid material based on a side reaction in a reaction mixture, i.e., humin ware filtered off, and a mixture produced by removing the solvent of the remaining solution under decompression was separated by the column chromatography (hexane:ethyl acetate=10:1→5:1) to thereby produce a mixture of 5-butoxymethyl-2-furfural and levulinic acid butyl ester at a yield of 20% (200 mg).

Exemplary Embodiment 4-3

Production of 5-butoxymethyl-2-furfural and Levulinic Acid Butyl Ester, with 20% Agar Solution 4 g of agar, 4 g of Dowex ion exchange resin as a solid acid catalyst, and 20 mL of n-butanol as a solvent and a reagent were put into a 250 mL round bottom flask and stirred to make suspension. Further, a reflux condenser was installed and temperature was slowly raised up to 90° C. Then, the suspension was stirred at 240 rpm, and reacted for 30 hours. At this time, colorless solution was changed to be brown (when about 4 to 5 hours elapse after the reaction initiation). After the reaction, a solid acid catalyst and a solid material based on a side reaction in a reaction mixture, i.e., humin ware filtered off, and a mixture produced by removing the solvent of the remaining solution under decompression was separated by the column chromatography (hexane:ethyl acetate=10:1→5:1) to thereby produce a mixture of 5-butoxymethyl-2-furfural and levulinic acid butyl ester at a yield of 20% (800 mg), which was ascertained through NMR (see FIG. 7).

Figure 7:
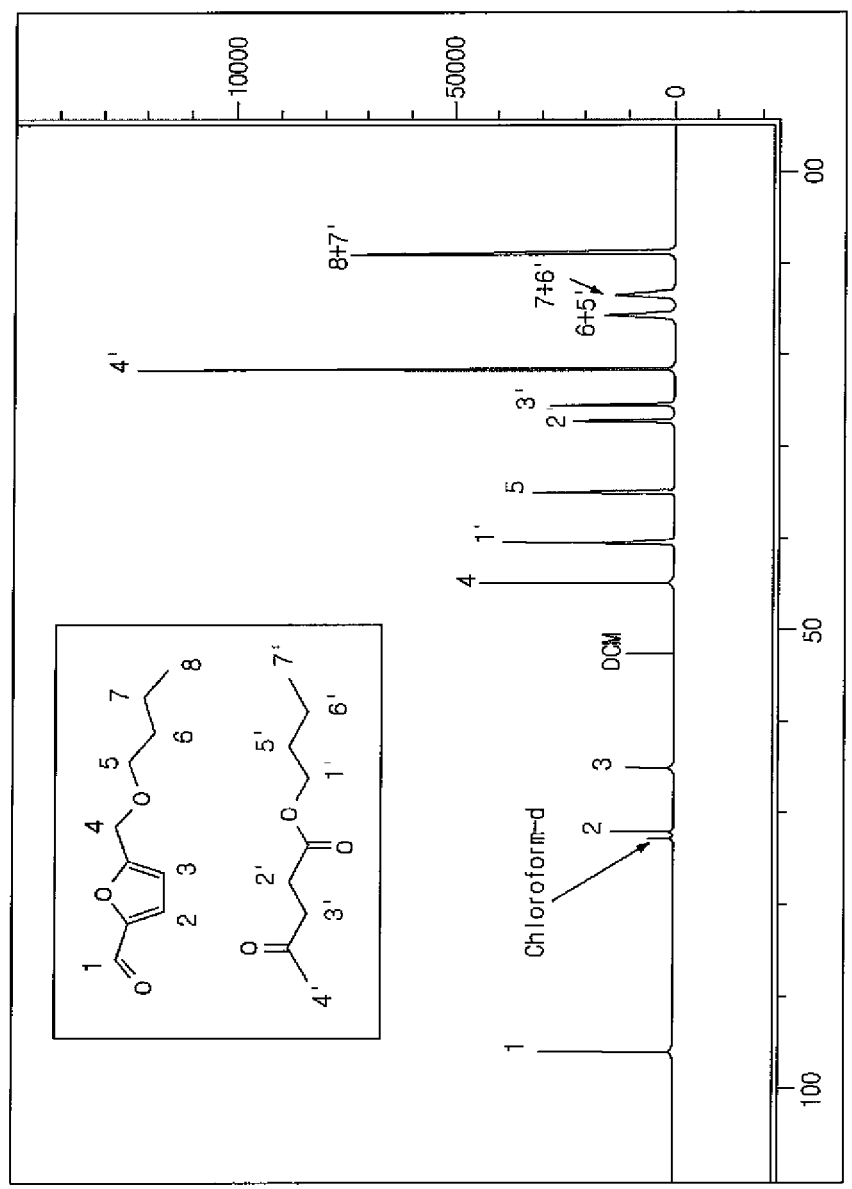
FIG. 7 is a view showing $^1H$-NMR of a mixture between levulinic acid butyl ester and 5-butoxymethyl-2-furfural obtained after being separated and refined by applying column chromatography to a product material according to an exemplary embodiment 4-3, in which location of a proton corresponding to each material is represented as a numeral.

FIG. 7 is a view showing $^1$H-NMR of a mixture between levulinic acid butyl ester and 5-butoxymethyl-2-furfural obtained after a material produced from agar is separated and refined by the column chromatography through the solid acid catalyst conversion process under the ethanol solvent, in which location of a proton corresponding to each material is represented with a numeral.

As described above, according to an exemplary embodiment, the macroalgae of the marine biomass resources is used so that a carbon source can be more easily extracted than that of a lignocellulosic biomass resource without a problem of having an effect on grain price like a crop-based biomass.

Also, according to an exemplary embodiment, there are provided alternative fuel which can replace bio ethanol having lower energy density than the existing oil fuel, and bio fuel containing a platform key intermediate, which can replace oil-based aromatic compounds.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of preparing bio fuel from algal galactan, the method comprising:
obtaining galactan, wherein the galactan has been extracted as a polysaccharide from marine algae, further wherein the galactan comprises agar; and
carrying out reaction for preparing bio fuel comprising at least one of 5-hydroxymethyl-2-furfural (HMF) and 5-alkoxymethyl-2-furfural (AMF) represented by the following chemical formula I

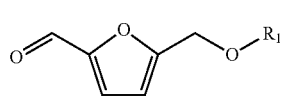

[Chemical formula I]

where, $R_1$ is one of hydrogen, alkyl, alkenyl, alkynyl, cycloalkyl and aryl groups through a catalyst conversion reaction using the galactan by adding the galactan into a solvent together with at least one of an organic acid catalyst, an inorganic acid catalyst, a solid acid catalyst, or a metal catalyst, wherein a ratio of the galactan to the solvent ranges from 0.5 g/L to 50 g/L.

2. The method according to claim 1, wherein the bio fuel comprises levulinic acid alkyl ester represented by the following chemical formula II

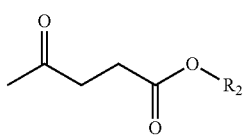

[Chemical formula II]

where, $R_2$ is one of alkyl, alkenyl, alkynyl, cycloalkyl and aryl groups.

3. The method according to claim 1, wherein the marine algae comprises macroalgae.

4. The method according to claim 1, wherein the metal catalyst is represented by MXn or MXn.H$_2$O (where, M is a metallic element, X is selected from a functional group consisting of halogen or triflate, nonaflate, mesylate, tosylate or diazonium, and n is 1 to 3).

5. The method according to claim 4, wherein the metallic element is selected from a group consisting of Mn, Ni, Fe, Cr, Cu, Co, Ru, Zn, Al, Ce, La, Nd, Sc, Yb and In.

6. The method according to claim 1, wherein the catalyst comprises a mixture of a Brønsted acid cation exchange resin catalyst as the solid acid catalyst and CrCl$_2$ as the metal catalyst.

7. The method according to claim 1, wherein the metal catalyst is represented by the following chemical formula III, and is a heterogeneous catalyst that comprises a solid imidazole ligand consisting of a high molecular resin and an imidazole compound, in which a metallic element is coordinated to the imidazole ligand

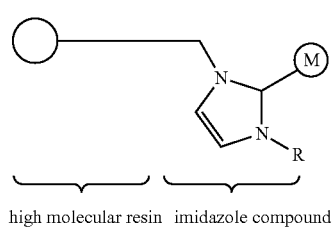

[Chemical formula III]

high molecular resin   imidazole compound where, R is an alkyl or methyl group that contains or does not contain a hetero atom, and M is a metallic element.

8. The method according to claim 7, wherein the high molecular resin comprises a polystyrene resin.

9. The method according to claim 7, wherein the metallic element is selected from a group consisting of transition metal, alkali metal, lanthanide metal, and mercury (Hg).

10. The method according to claim 1, wherein the solvent comprises at least one of alcohol, ionic liquid and an aprotic polar solvent.

11. The method according to claim 1, wherein the reaction is carried out at a reaction temperature of 50 to 200° C.

12. The method according to claim 11, wherein the reaction is carried out for 1 to 50 hours.

* * * * *

UNITED STATES PATENT AND TRADEMARK OFFICE
CERTIFICATE OF CORRECTION

| | | |
|---|---|---|
| PATENT NO. | : 8,795,393 B2 | |
| APPLICATION NO. | : 13/320058 | |
| DATED | : August 5, 2014 | |
| INVENTOR(S) | : Jin-Ku Cho et al. | |

It is certified that error appears in the above-identified patent and that said Letters Patent is hereby corrected as shown below:

ON THE TITLE PAGE

The following reference needs to be added in the References Cited - Foreign Patent Documents section of the patent:

GB 171,479

Signed and Sealed this
Twenty-fourth Day of May, 2016

Michelle K. Lee
*Director of the United States Patent and Trademark Office*